United States Patent
Madan et al.

(10) Patent No.: US 11,608,359 B2
(45) Date of Patent: *Mar. 21, 2023

(54) COMPOUNDS AND METHODS FOR TREATING TIGHT JUNCTION PERMEABTILITY

(71) Applicant: 9 Meters Biopharma, Inc., Raleigh, NC (US)

(72) Inventors: Jay P. Madan, Raleigh, NC (US); Balasingham Radhakrishnan, Raleigh, NC (US); Sandeep Laumas, Raleigh, NC (US); Christopher Prior, Raleigh, NC (US)

(73) Assignee: 9 Meters Biopharma, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/971,739

(22) PCT Filed: Feb. 25, 2019

(86) PCT No.: PCT/US2019/019350
§ 371 (c)(1),
(2) Date: Aug. 21, 2020

(87) PCT Pub. No.: WO2019/165346
PCT Pub. Date: Aug. 29, 2019

(65) Prior Publication Data
US 2020/0392186 A1    Dec. 17, 2020

Related U.S. Application Data

(60) Provisional application No. 62/634,536, filed on Feb. 23, 2018.

(51) Int. Cl.
C07K 7/08      (2006.01)
A61P 1/00     (2006.01)
A61K 38/00    (2006.01)

(52) U.S. Cl.
CPC .............. C07K 7/08 (2013.01); A61P 1/00 (2018.01); A61K 38/00 (2013.01)

(58) Field of Classification Search
CPC .............. C07K 7/08; A61P 1/00; A61K 38/00
See application file for complete search history.

(56) References Cited

U.S. PATENT DOCUMENTS

| | | |
|---|---|---|
| 5,945,510 A | 8/1999 | Fasano |
| 6,458,925 B1 | 10/2002 | Fasano |
| 6,670,448 B2 | 12/2003 | Fasano |
| 6,936,689 B2 | 8/2005 | Fasano |
| 7,026,294 B2 | 4/2006 | Fasano et al. |
| 7,189,696 B2 | 3/2007 | Fasano |
| 7,531,504 B2 | 5/2009 | Fasano |
| 7,531,512 B2 | 5/2009 | Fasano et al. |
| 7,582,603 B2 | 9/2009 | Fasano |
| 8,034,776 B2 | 10/2011 | Fasano et al. |
| 8,168,594 B2 | 5/2012 | Paterson et al. |
| 8,183,211 B2 | 5/2012 | Fasano |
| 8,198,233 B2 | 6/2012 | Tamiz et al. |
| 8,299,017 B2 | 10/2012 | Paterson et al. |
| 8,557,763 B2 | 10/2013 | Tamiz et al. |
| 8,728,491 B2 | 5/2014 | Sesardic et al. |
| 8,785,374 B2 | 7/2014 | Tamiz |
| 8,796,203 B2 | 8/2014 | Paterson et al. |
| 8,957,032 B2 | 2/2015 | Alkan et al. |
| 9,051,349 B2 | 6/2015 | Callens et al. |
| 9,241,969 B2 | 1/2016 | Paterson et al. |
| 9,265,811 B2 | 2/2016 | Paterson et al. |
| 9,279,807 B2 | 3/2016 | Fasano et al. |
| 10,526,372 B2 | 1/2020 | Alkan et al. |
| 10,723,763 B2 | 7/2020 | Paterson et al. |
| 11,058,902 B2* | 7/2021 | Madan ............ C07K 7/06 |
| 11,149,063 B2 | 10/2021 | Alkan et al. |
| 2002/0115825 A1* | 8/2002 | Fasano ............ C07K 7/06 530/324 |
| 2004/0077540 A1 | 4/2004 | Quay |
| 2006/0287233 A1 | 12/2006 | Fasano et al. |
| 2007/0196501 A1 | 8/2007 | Paterson et al. |
| 2008/0103100 A1* | 5/2008 | Fasano ............ A61P 3/00 514/21.7 |
| 2010/0280221 A1 | 11/2010 | Callens et al. |

(Continued)

FOREIGN PATENT DOCUMENTS

| | | |
|---|---|---|
| WO | 20007609 | 2/2000 |
| WO | 2008150981 | 12/2008 |

(Continued)

OTHER PUBLICATIONS

Rink et al., 2010, To protect peptide pharmaceuticals against peptidases, Journal of Pharmacological and Toxicological Methods, 61: 210-218.*
Freeman, 2014, Emerging drugs for celiac disease, Expert Opin Emerging Drugs, 20(1): 129-135.*
Veeraraghavan et al., 2015, Celiac disease 2015 update: new therapies, Expert Rev Gastroenterol Hepatol, 9(7): 913-927.*
Kurada et al., 2016, Current and novel therapeutic strategies in celiac disease, Expert Rev of Clinical Pharmacology, 9(9): 1211-1223.*
Silva et al., 2012, Increased Bacterial Translocation in Gluten-Sensitive Mice Is Independent of Small Intestinal Paracellular Permeability Defect, Dig Dis Sci, 57(1): 38-47.*
Paterson et al., 2007, The safety, tolerance, pharmacokinetic and pharmacodynamics effects of single doses of AT-1001 in coeliac disease subjects: a proof of concept study, Aliment Pharmacol Ther, 26: 757-766.*

(Continued)

*Primary Examiner* — Amber D Steele
(74) *Attorney, Agent, or Firm* — Morgan, Lewis & Bockius LLP

(57) ABSTRACT

The present invention provides Larazotide derivative compositions that resist protease degradation, and in various embodiments, do not demonstrate an inverse dose response, and/or can be delivered at higher doses without loss of potency or efficacy, thereby allowing improved therapy and more desirable dosing schedules.

18 Claims, No Drawings
Specification includes a Sequence Listing.

(56) References Cited

U.S. PATENT DOCUMENTS

| | | | |
|---|---|---|---|
| 2011/0077191 A1* | 3/2011 | Tamiz | A61K 38/06 514/1.5 |
| 2011/0142881 A1 | 6/2011 | Sesardic et al. | |
| 2011/0275562 A1* | 11/2011 | Alkan | C07K 5/0817 530/331 |
| 2012/0076861 A1 | 3/2012 | Fasano et al. | |
| 2013/0281384 A1* | 10/2013 | Callens | C07K 7/06 514/21.7 |
| 2015/0164978 A1 | 6/2015 | Paterson et al. | |
| 2016/0022760 A1* | 1/2016 | Perrow | A61P 3/00 514/21.7 |
| 2019/0358288 A1 | 11/2019 | Madan et al. | |
| 2021/0030814 A1 | 2/2021 | Madan | |
| 2021/0100868 A1 | 4/2021 | Blikslager | |
| 2021/0169968 A1 | 6/2021 | Madan et al. | |
| 2021/0236586 A1 | 8/2021 | Madan et al. | |
| 2021/0299481 A1 | 9/2021 | Madan et al. | |

FOREIGN PATENT DOCUMENTS

| | | |
|---|---|---|
| WO | 2015154010 | 10/2015 |
| WO | 2019183036 | 9/2019 |
| WO | 2020227341 | 11/2020 |

OTHER PUBLICATIONS

Perez et al., 2012, Non-dietary therapeutic clinical trials in coeliac disease, European Journal of Internal Medicine, 23: 9-14.*

Gopalakrishnan et al., 2012, Larazotide acetate regulates epithelial tight junctions in vitro and in vivo, Peptides, 35: 86-94.*

Kelly et al., 2013, Larazotide acetate in patients with coeliac disease undergoing a gluten challenge: a randomized placebo-controlled study, Aliment Pharmacol Ther, 37: 252-262.*

Vanga et al., 2014, Novel Therapeutic Approaches for Celiac Disease, Discovery Medicine, 17(95): 285-293.*

Szaflarska-Poplawska, 2015, Non-dietary methods in the treatment of celiac disease, Prz Garstroenterol, 10(1): 12-17.*

Leffler et al., 2012, A Randomized, Double-Blind Study of Larazotide Acetate to Prevent the Activation of Celiac Disease During Gluten Challenge, Am J Gastroenterol, 107: 1554-1562.*

Leffler et al., 2015, Larazotide Acetate for Persistant Symptoms of Celiac Disease Despite a Gluten-Free Diet: A Randomized Controlled Trial, Gastroenterology, 148(7): 1311-1319.*

McCarville et al., 2015, Pharmacological approaches in celiac disease, Current Opinion in Pharmacology, 25: 7-12.*

Khaleghi et al., 2016, The potential utility of tight junction regulation in celiac disease: focus on larazotide acetate, Therapeutic Advances in Gastroenterology, 9(1): 37-49.*

Yang et al., 2017, Novel Insights into Microbiome in Colitis and Colorectal Cancer, Curr Opin Gastroenterol, 33(6): 422-427.*

Arrieta et al., 2009, Reducing small intestinal permeability attenuates colitis in the IL10 gene-deficient mouse, Gut, 58: 41-48.*

Gopalakrishnan, et al., "Larazotide acetate promotes tight junction assembly in epithelial cells". Peptides, 2012, vol. 35, No. 1: pp. 95-101. Abstract only.

Makharia, "Current and emerging therapy for celiac disease". Frontiers in Medicine, 2014, vol. 1, No. 6; article 6, pp. 1-11.

International Search Report and Written Opinion for International Application No. PCT/US2019/019350, dated Jul. 10, 2019, 15 pages.

Arrieta, et al., "Alterations in Intestinal Permeability", Gut, Oct. 2006, vol. 55, No. 10, pp. 1512-1520.

International Search Report issued in Appl. No. PCT/US2009/042973 dated Dec. 15, 2009, 5 pages.

McGregor, "Discovering and improving novel peptide therapeutics", Current Opinion in Pharmacology 2008, 8:616-619.

Holmes, et al., "Intestinal brush border revisited", Gut, 1989, 30, 1667-1678.

* cited by examiner

COMPOUNDS AND METHODS FOR TREATING TIGHT JUNCTION PERMEABTILITY

FIELD OF THE INVENTION

The present invention provides compositions and methods for treating conditions associated with a lack of tight junction integrity, including of the intestinal epithelium.

CROSS-REFERENCE TO RELATED APPLICATIONS

This application is a National Stage Entry of PCT/US2019/019350, filed Feb. 25, 2019, which claims priority to U.S. Provisional Application No. 62/634,536, filed on Feb. 23, 2018, the contents of which are hereby incorporated in their entirety.

The claimed invention was made by, or on behalf of, one or more of the following parties to a joint research agreement: Innovate Biopharmaceuticals, Inc. (now 9 Meters Biopharma, Inc.) and North Carolina State University. The agreement was in effect on and before the date the claimed invention was made, and the claimed invention was made as a result of activities undertaken within the scope of the agreement.

BACKGROUND

The intestinal epithelium is the layer of cells that forms the luminal surface of the small and large intestines of the gastrointestinal (GI) tract, and represents the largest interface (more than 400 m$^2$) between the external environment and the internal milieu. The intestinal epithelium has two important functions: absorbing nutrients and providing a barrier against harmful environmental substances such as bacteria, viruses, toxins, and food allergens.

The barrier properties of the intestinal epithelium are regulated by specialized plasma membrane structures known as tight junctions. Alterations in tight junctions can result in disruptions of the intestinal barrier functions and increased intestinal permeability. An intact intestinal barrier prevents the permeation of pathogens, antigens, endotoxins, and other proinflammatory substances into the body, whereas intestinal disintegrity allows their entry, which may trigger or exacerbate local or systemic inflammatory disease.

Larazotide is a peptide agent that promotes tight junction integrity. Larazotide has the amino acid sequence: Gly Gly Val Leu Val Gln Pro Gly (SEQ ID NO:1), and can be formulated for targeted release in affected portions of the GI (e.g., small intestine and/or large intestine) or delivered to other tissues that exhibit reduced integrity of tight junctions. Larazotide has been described as exhibiting an inverse dose response, where higher doses show an attenuated activity or no activity at all. This inverse dose response may limit the overall efficacy of the drug and requires undesirable dosing schedules.

DESCRIPTION OF THE INVENTION

The present invention provides Larazotide derivative compositions that resist protease degradation, and in various embodiments, do not demonstrate an inverse dose response, and/or can be delivered at higher doses without loss of potency or efficacy, thereby allowing improved therapy and/or more desirable dosing schedules.

"Larazotide" is an eight amino acid peptide that has the sequence GGVLVQPG (SEQ ID NO:1), alternatively depicted using the formula G1-G2-V3-L4-V5-Q6-P7-G8 (SEQ ID NO:1) to indicate amino acid sequence numbering. Larazotide, when formulated as the salt with acetic acid, is Larazotide acetate. Larazotide functions promotes tight junction integrity, including of the intestinal epithelium, and is being evaluated as a therapy for patients with celiac disease (CeD).

In accordance with certain embodiments, the present invention provides Larazotide derivatives having various amino acid modifications that confer increased resistance to exopeptidase degradation, including aminopeptidase degradation. A protease or peptidase is an enzyme that catalyzes the hydrolytic degradation of peptide bonds. Peptidases can be exopeptidases or endopeptidases. An exopeptidase catalyzes the cleavage of the terminal or penultimate peptide bond. Depending on whether the amino acid is released from the amino or the carboxy terminus, an exopeptidase is further characterized as an aminopeptidase or a carboxypeptidase, respectively. An aminopeptidase, such as an enzyme found in the brush border of the small intestine, will cleave one or more amino acids from the amino terminus of the peptide. A carboxypeptidase, such as an enzyme present in the digestive pancreatic juice, will cleave one or more amino acids from the carboxylic end of the peptide. A peptide can undergo multiple rounds of N- or C-terminal cleavage.

Larazotide has been shown in clinical trials to exhibit significant benefit at reducing CeD symptoms, particularly at the lower doses (e.g., 0.5 mg dose). See US 2016/0022760, which is hereby incorporated by reference in its entirety, and in particular for the formulations and dosages outlined therein. Higher doses (e.g., 1 mg and 2 mg doses) showed an attenuation of activity, or no activity at all. In accordance with this disclosure, it is believed that an aminopeptidase located within the brush borders of the lumen surface may create Larazotide-derived fragments, including fragments missing N-terminal glycine residues. For example, the fragments GVLVQPG (SEQ ID NO:2) and VLVQPG (SEQ ID NO:3) are inactive as tight junction regulators. Moreover, when these two fragments are mixed with full length Larazotide, activity is completely abolished. Local buildup of these inactive Larazotide fragments (due to excessive doses of Larazotide) may in fact compete and block function of the peptide. This would explain clinical observations that low doses of Larazotide work best by avoiding the reservoir of competing inactive fragments.

The present invention provides compounds that promote tight junction integrity (e.g., epithelial or endothelial tight junction integrity), and which exhibit resistance to exopeptidases, such as aminopeptidases. In some embodiments, administering the pharmaceutical compositions of the present invention to patients in need, avoids substantial accumulation of inactive peptide fragments such as GVLVQPG (SEQ ID NO:2), VLVQPG (SEQ ID NO:3), VLVQP (SEQ ID NO:4), and GVLVQP (SEQ ID NO:5). In various embodiments, the peptides of the present invention are derivatives of Larazotide with one or more amino acid modifications that reduce or inhibit exopeptidase activity on the peptide. These modifications include amino acid substitutions at the N- and/or C-terminus to reduce exopeptidase digestion, extension of the N- and/or C-termini to delay exopeptidase digestion of the functional peptide, incorporation of D amino acids, as well as cyclization.

In various embodiments, the peptide comprises the amino acid sequence of SEQ ID NO:1, with one or two substitutions (at one or both of the N- and C-termini) of an amino acid having a different side chain, so as to reduce proteolytic susceptibility. In some embodiments, the peptide comprises amino acid substitutions for one or both of the N-terminal glycine residues, and optionally for the C-terminal Gly, or optionally for the two C-terminal amino acid residues. The amino acid substitutions may be a genetically-encoded or a non-genetically-encoded amino acid, and which are each optionally D-amino acids.

In various embodiments, the substitutions comprise non-polar amino acids, and/or amino acids with bulky side chains. Exemplary substitutions at the N- and/or C-terminus include amino acids selected from alanine (A), histidine (H), isoleucine (I), leucine (L), methionine (M), phenylalanine (F), proline (P), tryptophan (W), tyrosine (Y), and valine (V). Non-genetically encoded amino acids include N-methyl amino acids, allylglycine, selenocysteine, pyrrolysine, N-formylmethionine, β-amino acids such as β-alanine, GABA, δ-Aminolevulinic acid, 4-aminobenzoic acid (PABA), 2,4-diaminobutyric acid, α-amino isobutyric acid, 4-aminobutyric acid, 2-amino butyric acid, γ-Abu, ε-Ahx, 6-amino hexanoic acid, 2-amino isobutyric acid, 3-amino propionic acid, ornithine, norleucine, norvaline, hydroxy-proline, sarcosine, citrulline, homocitrulline, cysteic acid, t-butylglycine, t-butylalanine, phenylglycine, homo-amino acids such as homophenylalanine, cyclohexylalanine, and fluoro-amino acids (such as fluoro-substituted phenylalanine or tyrosine). In various embodiments, the amino acid substitution(s) are selected from alanine, valine, isoleucine, leucine, norleucine, norvaline, and allylgly.

In some embodiments, the peptide comprises a substitution of an amino acid (e.g., a substitution of one or more N-terminal Gly residues, and/or the C-terminal Gly residue) with a charged side chain. In some embodiments one or both of the N terminal glycine residues are replaced with an amino acid having a charged side chain. Amino acids with negatively charged side chains include aspartic acid (D) and glutamic acid (E). Amino acids with positively charged side chains include lysine (K), arginine (R), and histidine (H).

In exemplary embodiments, a methionine (M) replaces one or both of the N terminal glycine residues of SEQ ID NO:1.

In some embodiments, the peptide has a single amino acid addition at the N-terminus to prevent or slow aminopeptidase action. While any amino acid other than Gly could be employed, exemplary peptides in these embodiments include MGGVLVQPG (SEQ ID NO:6), HGGVLVQPG (SEQ ID NO:7), FGGVLVQPG (SEQ ID NO:8), and LGGVLVQPG (SEQ ID NO:9). Exemplary peptides have the formula X1-G2-G3-V4-L5-V6-Q7-P8-G9 (SEQ ID NO:10), where X is a genetically-encoded or non-genetically encoded amino acid other than Gly. In some embodiments, X may be alanine, valine, isoleucine, leucine, norleucine, norvaline, and allylgly, and may optionally be a D-amino acid.

In various embodiments, the peptide comprises amino acid substitutions of at least one of the N terminal glycine residues (and the substitution may optionally be a D-amino acid), optionally in combination with a C-terminal extension of from 1 to 8 amino acids, such as C-terminal extensions of 2, 3, 4, or 5 amino acids. Some exemplary embodiments include, X1-G2-V3-L4-V5-Q6-P7-G8 (SEQ ID NO:11), G1-X2-V3-L4-V5-Q6-P7-G8 (SEQ ID NO:12), X1-X2-V3-L4-V5-Q6-P7-G8 (SEQ ID NO:13), X1-G2-V3-L4-V5-Q6-P7-G8-X9-X10 (SEQ ID NO:14), and X1-X2-V3-L4-V5-Q6-P7-G8-X9-X10 (SEQ ID NO:15) wherein X is an independently selected genetically-encoded or non-genetically-encoded amino acid, such as an amino acid selected from A, S, T, W, F, I, L, K, M, C, P, N, Q, E, D, R, H, V, and Y). In some embodiments, the C-terminal extension amino acid(s) comprise one or more Gly residues.

In these or other embodiments, the peptide comprises an addition of amino acid(s) to the N- and/or C-terminus with respect to the peptide of SEQ ID NO:1. The addition of at least one amino acid to the N terminus and/or C-terminus may confer resistance by delaying exopeptidase degradation because said exopeptidase would have a longer stretch of amino acids to digest, thus delaying the formation of the inactive fragments.

In various embodiments, the N- and/or C-terminal extension amino acids may be selected from non-polar amino acids and/or amino acids with bulky side chains. Exemplary substitutions at the N- and/or C-terminus include one or more of Ala, His, Ile, Leu, Met, Phe, Pro, Trp, Tyr, and Val. Non-genetically encoded amino acid useful in these embodiments include N-methyl amino acids, allylglycine, selenocysteine, pyrrolysine, N-formylmethionine, β-amino acids such as β-alanine, GABA, Aminolevulinic acid, 4-aminobenzoic acid (PABA), 2,4-diaminobutyric acid, α-amino isobutyric acid, 4-aminobutyric acid, 2-amino butyric acid, γ-Abu, ε-Ahx, δ-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, homo-amino acids such as homophenylalanine, cyclohexylalanine, and fluoro-amino acids (such as fluoro-substituted phenylalanine or tyrosine). In various embodiments, the amino acid substitution(s) are selected from alanine, valine, isoleucine, leucine, norleucine, norvaline, and allylgly.

In various embodiments of the present invention, at least one, at least 2, at least 3, at least 4, at least 5, at least 6, at least 7, at least 8, at least 9, or at least 10 amino acids are added to the N and/or C terminus, with respect to SEQ ID NO:1. In an embodiment, the peptide comprises the addition of at least one amino acid to both the N and C termini with respect to SEQ ID NO:1, and the additional amino acid residues are optionally D-amino acids.

In an embodiment, the peptide comprises the addition of at least 2 glycine residues to the N or C terminus with respect to SEQ ID NO:1. For example, the peptide may comprise the formula (GG)$_n$GGVLVQPG, where n=1 to 10 (SEQ ID NO: 16), and where n is optionally 2, 3, 4, or 5.

In some aspects, the invention provides the compounds of SEQ ID NO:1 having one or more D-amino acids. D-amino acids are rarely found in nature, and exopeptidases, in general, have difficulty recognizing D-amino acids as a substrate. Accordingly, compositions comprising at least one D-amino acid may provide for the same amino acid sequence but in a left-handed configuration, as opposed to L-amino acids in the right-handed configuration. In various embodiments, peptides of the present invention comprising at least one D-amino acid at the N- or C-terminus confer increased resistance to exopeptidase degradation by exopeptidases, and in particular, aminopeptidases. In some embodiments, the peptide exhibits increased resistance to degradation as compared to Larazotide.

In various embodiments, the peptide has at least one, at least two, at least three, at least four, at least five, at least six, at least seven, or at least eight D-amino acids. In an embodiment, each amino acid of the Larazotide derivative (other than Gly) is a D-amino acid, and is optionally a retro-inverso peptide. A retro-inverso peptide contains the inverse amino acid sequence (e.g., GPQVLVGG, SEQ ID NO:17), with all non-glycine amino acids present as D-amino acids. Retro-inverso peptides maintain side chain topology similar to that of the original L-amino acid peptide, and render the peptide more resistant to proteolytic degradation. In some embodiments, the N-terminal Gly of the retro-inverso peptide is substituted with Ala, Leu, Ile, Val, or Allylgly. In these or other embodiments, one or both of the C-terminal Gly residues of the retro inverso peptide is/are substituted with an amino acid independently selected from Ala, Leu, Ile, Val, or Allylgly.

In other embodiments, the peptide having the amino acid sequence of SEQ ID NO:1 has one or two D-amino acids at the N- and optionally the C-terminus, with all other amino acids in the L configuration. In these embodiments, the N- and/or C-terminus are substituted or extended such that the peptide does not have a glycine at the terminus (Gly does not have D- and L-configurations). In some embodiments, the terminal Gly residues are replaced with D-Ala.

D-amino acids are depicted herein using "(d)" to indicate that the following amino acid in the D conformation. Accordingly, exemplary peptides in accordance with these aspects of the invention include: (d)X1-G2-V3-L4-V5-Q6-P7-G8 (SEQ ID NO:18), G1-G2-V3-L4-V5-Q6-P7-(d)X8 (SEQ ID NO:19), (d)X1-(d)X2-V3-L4-V5-Q6-P7-G8 (SEQ ID NO:20), (d)X1-G2-V3-L4-V5-Q6-P7-(d)X8 (SEQ ID NO:21), (d)X1-(d)G2-V3-L4-V5-Q6-P7-(d)X8 (SEQ ID NO:22), and (d)X1-(d)X2-V3-L4-V5-Q6-(d)P7-(d)X8 (SEQ ID NO:23), where X is an independently selected genetically or non-genetically-encoded amino acid other than Gly. In some embodiments, X is a cyclic side chain for one or both of the N terminal glycine residues of SEQ ID NO:1, such as phenylalanine, tyrosine, histidine, proline, or tryptophan.

In these or other embodiments, the peptide is a cyclized derivative of Larazotide, which can be synthesized using chemical moieties (using well known F-moc chemistries, for example) as well as by the incorporation of amino acid residues with functional groups that allow cyclization, such as cysteine residues that spontaneously form disulfide bonds to cyclize peptides or synthetic amino acids that permit covalent cyclization. See C. White and A. Yudin, (2011) Nature Chemistry 3: 509-524, the entire contents of which are hereby incorporated by reference, specifically with regards to general peptide cyclization method considerations.

Thus, in some embodiments, cyclized Larazotide derivatives are synthesized to include at least two amino acid modifications so that a covalent linkage, such as a disulfide bond in the case of cysteine residues, is formed in order to confer increased resistance to exopeptidase degradation, particularly aminopeptidase degradation.

In some embodiments, the peptide is cyclized using reactive groups at or near the N- and/or C-terminus of the peptide, and using any available chemistry. In various embodiments, the peptide comprises an amino acid substitution or extension on the N- and/or C-terminus having a chemically reactive side chain such that a covalent bond (e.g., a disulfide bond in the case of Cysteines) can be formed, either spontaneously or with the addition of a chemically reactive reagent (which can be a bivalent reagent in some embodiments, and may contain an alkyl linker structure). The amino acid modifications may comprise insertions or additions of said cysteine residues, or other amino acid having a chemically reactive side chain, such as a hydroxyl, amine, amide, or sulfhydryl. In other embodiments, a cyclized Larazotide derivative is formed by introducing at least two synthetic amino acids with side chains that facilitate covalent linkage. Accordingly, these embodiments can exploit the glycine residues that will allow the peptide to bend, thus bringing into close proximity the N- and C-terminal ends, thereby facilitating a covalent linkage to form.

Specific embodiments include, but are not limited to, G1-G2-C-V3-L4-V5-Q6-P7-G8 (SEQ ID NO:24), (n-1)C-G1-G2-V3-L4-V5-Q6-P7-G8-9C (SEQ ID NO:25) and (n-3)C-(n-2)G-(n-1)G-G1-G2-V3-L4-V5-Q6-P7-G8-9C (SEQ ID NO:26).

In various embodiments, the peptide exhibits increased resistance to peptidase degradation as compared to the peptide of SEQ ID NO:1. The degree of resistance can be quantified using any suitable peptidase activity assay. One of skill in the art will appreciate the various quantitative and qualitative methods in which protein degradation may be measured in order to determine susceptibility to peptidase activity. In some embodiments, the peptide demonstrates resistance to aminopeptidase activity, and in some embodiments, a human aminopeptidase found in the brush borders of the human lumen surface. In some embodiments, the peptide demonstrates resistance to a carboxypeptidase, such as a human carboxypeptidase.

In various embodiments, the invention provides methods for promoting tight junction integrity of a tissue, including tight junction integrity of epithelial or endothelial cells, by administering a peptide or composition described herein. In some embodiments, the peptide or composition is administered to the gastrointestinal tract (GI) to prevent or reduce gastrointestinal inflammation. Compositions can be formulated for targeted release in affected portions of the GI (e.g., small intestine and/or large intestine). In other embodiments, Larazotide is administered systemically (e.g., intravenously or by subcutaneous injection). In some embodiments, the peptide composition is administered to the lungs as a solution aerosol or powder.

In various embodiments, the composition is formulated to have a delayed-release profile, i.e. targeted release of the Larazotide derivatives in the GI tract. The delayed-release profile allows for the Larazotide derivate to not be immediately released upon ingestion; but rather, there is a postponement of the release until the composition is lower in the gastrointestinal tract. The derivative can be formulated for release in the small intestine (e.g., one or more of duodenum, jejunum, and ileum) and/or the large intestine (e.g., one or more of cecum, ascending, transverse, descending or sigmoid portions of the colon, and rectum). In an embodiment, the pharmaceutical composition is formulated to have a delayed-release profile as described in, for example, U.S. Pat. No. 8,168,594, the entire contents of which are hereby incorporated by reference.

In various embodiments, the compositions of the present invention may use one or more modified-release coatings such as delayed-release coatings to provide for effective, delayed yet substantial delivery of the peptide to the GI tract. For example, a composition can be enteric coated to delay release of the peptide until it reaches the small intestine or the large intestine.

In some embodiments, the subject has celiac disease, and the peptide is formulated for targeted release in the small intestine, including the duodenum and jejunum (and optionally the ileum). Methods of treatment with Larazotide formulations are disclosed US 2016/0022760, which is hereby incorporated by reference in its entirety.

In some embodiments, the invention provides a method for treating Inflammatory Bowel Disease, such as Crohn's Disease or Ulcerative Colitis, by administering the peptides of the present invention, formulated for delivery to affected portions of the GI.

In some embodiments, the invention provides methods of treating other conditions of the gastrointestinal tract, such as environmental enteropathy or necrotizing enterocolitis, by administering the peptides of the present invention formulated for delivery to the GI.

In still other embodiments, the invention provides methods for treating leaky gut, or methods for improving tight junction integrity of the intestinal epithelium, including in patients having or at risk of inflammatory liver disease, such as non-alcoholic fatty liver disease (NAFLD), non-alcoholic steatohepatitis (NASH), or a fatty liver disease resulting from hepatitis, obesity, diabetes, insulin resistance, hypertriglyceridemia, abetalipoproteinemia, glycogen storage disease, Weber-Christian disease, Wolmans disease, acute fatty liver of pregnancy, and liver regeneration.

In some embodiments, the subject has chronic kidney disease, which can be Stage 1, Stage 2, Stage 3, or Stage 4. Kidney disease can manifest from small changes in kidney function, resulting in low glomerular filtration rate (GFR) measured in ml/min/1.73 $m^2$, which can eventually lead to loss of kidney function and/or kidney failure. In some embodiments, patients with Stage 1 chronic kidney disease have a GFR of 90 ml/min/1.73 $m^2$ or higher, indicating kidney damage with normal kidney function; patients with Stage 2 chronic kidney disease have a GFR of 89 to 60 ml/min/1.73 $m^2$, indicating kidney damage with mild loss of kidney function; patients with Stage 3a chronic kidney disease have a GFR of 59 to 45 ml/min/1.73 $m^2$, indicating mild to moderate loss of kidney function; patients with Stage 3b chronic kidney disease have a GFR of 44 to 30 ml/min/1.73 $m^2$, indicating moderate to severe loss of kidney function; patients with Stage 4 chronic kidney disease have a GFR of 29 to 15 ml/min/1.73 $m^2$, indicating severe loss of kidney function; and patients with Stage 5 chronic kidney disease have a GFR of less than 15 ml/min/1.73 $m^2$, indicating total loss of kidney function and/or kidney failure. In further embodiments, patients with chronic kidney disease exhibit high levels of serum creatinine.

In some embodiments, the peptide is formulated for pulmonary delivery or systemic delivery, and administered to subjects having or at risk of Acute Lung Injury (ALI) or Acute Respiratory Distress Syndrome (ARDS).

In some embodiments, the peptide is administered in unit dosage forms (e.g., tablets, capsules, or solutions), at higher than about 0.5 mg per unit dose, which can provide for improved efficacy as compared to a corresponding unit dose of Larazotide. For example, the peptide unit dose may be about 1 mg or more, or about 2 mg or more, or about 5 mg or more, or about 10 mg or more. Unit doses may be formulated for sustained release in some embodiments.

In some embodiments, unit doses are administered about 3 times daily. However, in some embodiments, the peptide has a longer half-life in vivo than Larazotide, and thus may have a more durable biological action. In some embodiments, the peptide composition is administered no more than twice per day on average, or no more than once per day on average.

Larazotide derivatives of the present invention may be administered in any suitable form, including as a salt. For example, peptides may be administered as an acetate salt. Alternative salts may be employed, including any pharmaceutically acceptable salt such as those listed in Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety.

In various embodiments, the peptides are formulated as pharmaceutical compositions, which can take the form of tablets, pills, pellets, capsules, capsules containing liquids, capsules containing multiparticulates, powders, solutions, emulsion, drops, suppositories, emulsions, aerosols, sprays, suspensions, delayed-release formulations, sustained-release formulations, controlled-release formulations, or any other form suitable for use.

In some embodiments, the pharmaceutical compositions are formulated as a composition adapted for parenteral administration. Dosage forms suitable for parenteral administration (e.g. intravenous, intramuscular, or intraperitoneal injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

The invention claimed is:

1. A method for promoting tight junction integrity of intestinal barrier in a subject exhibiting symptoms of intestinal barrier dysfunction, comprising administering to the small intestine of said subject a composition comprising a unit dose of at least 1 mg of the peptide of SEQ ID NO: 1, wherein each non-glycine amino acid is a D-amino acid, thereby ameliorating said intestinal barrier dysfunction.

2. The method of claim 1, wherein the peptide is formulated for targeted release in the small intestine.

3. The method of claim 1, wherein the subject has celiac disease, Inflammatory Bowel Disease, environmental enteropathy, necrotizing enterocolitis, inflammatory liver disease, fatty liver disease, non-alcoholic fatty liver disease (NAFLD), or non-alcoholic steatohepatitis (NASH).

4. The method of claim 3, wherein the subject has celiac disease.

5. The method of claim 3, wherein the subject has Inflammatory Bowel Disease.

6. The method of claim 3, wherein the subject has environmental enteropathy.

7. The method of claim 3, wherein the subject has necrotizing enterocolitis.

8. The method of claim 3, wherein the subject has inflammatory liver disease.

9. The method of claim 3, wherein the subject has fatty liver disease.

10. The method of claim 9, wherein the fatty liver disease results from hepatitis, diabetes, or insulin resistance.

11. The method of claim 3, wherein the subject has non-alcoholic fatty liver disease (NAFLD).

12. The method of claim 3, wherein the subject has non-alcoholic steatohepatitis (NASH).

13. The method of claim 1, wherein administering the peptide is at a unit dose comprising at least 2 mg of said peptide.

14. The method of claim 1, wherein administering the composition is less than 3 times daily.

15. The method of claim 14, wherein administering the composition is 2 times daily.

16. The method of claim 14, wherein administering the composition is 1 time daily.

17. The method of claim 1, wherein the subject has chronic kidney disease.

18. The method of claim 1, wherein the unit dose is formulated for sustained release.

* * * * *

SEQUENCE LISTING

```
<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 1

Gly Gly Val Leu Val Gln Pro Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polymer.
```

<400> SEQUENCE: 2

Gly Val Leu Val Gln Pro Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polymer.

<400> SEQUENCE: 3

Val Leu Val Gln Pro Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 4

Val Leu Val Gln Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic polymer.

<400> SEQUENCE: 5

Gly Val Leu Val Gln Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 6

Met Gly Gly Val Leu Val Gln Pro Gly
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 7

His Gly Gly Val Leu Val Gln Pro Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic polymer.

```
<400> SEQUENCE: 8

Phe Gly Gly Val Leu Val Gln Pro Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 9

Leu Gly Gly Val Leu Val Gln Pro Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(1)
<223> OTHER INFORMATION: X is a genetically-encoded or non-genetically
      encoded amino acid other than Gly, such as an amino acid selected
      from A, S, T, W, F, I, L, K, M, C, P, N, Q, E, D, R, H, V, and Y.

<400> SEQUENCE: 10

Xaa Gly Gly Val Leu Val Gln Pro Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(1)
<223> OTHER INFORMATION: X is a genetically-encoded or non-genetically
      encoded amino acid other than Gly, such as an amino acid selected
      from A, S, T, W, F, I, L, K, M, C, P, N, Q, E, D, R, H, V, and Y.

<400> SEQUENCE: 11

Xaa Gly Val Leu Val Gln Pro Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (2)..(2)
<223> OTHER INFORMATION: X is a genetically-encoded or non-genetically
      encoded amino acid other than Gly, such as an amino acid selected
      from A, S, T, W, F, I, L, K, M, C, P, N, Q, E, D, R, H, V, and Y.

<400> SEQUENCE: 12

Gly Xaa Val Leu Val Gln Pro Gly
1               5

<210> SEQ ID NO 13
<211> LENGTH: 8
<212> TYPE: PRT
```

```
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(2)
<223> OTHER INFORMATION: X is a genetically-encoded or non-genetically
      encoded amino acid other than Gly, such as an amino acid selected
      from A, S, T, W, F, I, L, K, M, C, P, N, Q, E, D, R, H, V, and Y.

<400> SEQUENCE: 13

Xaa Xaa Val Leu Val Gln Pro Gly
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(1)
<223> OTHER INFORMATION: X is a genetically-encoded or non-genetically
      encoded amino acid other than Gly, such as an amino acid selected
      from A, S, T, W, F, I, L, K, M, C, P, N, Q, E, D, R, H, V, and Y.
<220> FEATURE:
<221> NAME/KEY: X
<222> LOCATION: (9)..(10)
<223> OTHER INFORMATION: X is a genetically-encoded or non-genetically
      encoded amino acid other than Gly, such as an amino acid selected
      from A, S, T, W, F, I, L, K, M, C, P, N, Q, E, D, R, H, V, and Y.

<400> SEQUENCE: 14

Xaa Gly Val Leu Val Gln Pro Gly Xaa Xaa
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(2)
<223> OTHER INFORMATION: X is a genetically-encoded or non-genetically
      encoded amino acid other than Gly, such as an amino acid selected
      from A, S, T, W, F, I, L, K, M, C, P, N, Q, E, D, R, H, V, and Y.
<220> FEATURE:
<221> NAME/KEY: X
<222> LOCATION: (9)..(10)
<223> OTHER INFORMATION: X is a genetically-encoded or non-genetically
      encoded amino acid other than Gly, such as an amino acid selected
      from A, S, T, W, F, I, L, K, M, C, P, N, Q, E, D, R, H, V, and Y.

<400> SEQUENCE: 15

Xaa Xaa Val Leu Val Gln Pro Gly Xaa Xaa
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 16

Gly Gly Gly Gly Val Leu Val Gln Pro Gly
1               5                   10
```

```
<210> SEQ ID NO 17
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 17

Gly Pro Gln Val Leu Val Gly Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(1)
<223> OTHER INFORMATION: X is an independently selected genetically or
      non-genetically-encoded amino acid other than Gly, and in the D
      conformation.

<400> SEQUENCE: 18

Xaa Gly Val Leu Val Gln Pro Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (8)..(8)
<223> OTHER INFORMATION: X is an independently selected genetically or
      non-genetically-encoded amino acid other than Gly, and in the D
      conformation.

<400> SEQUENCE: 19

Gly Gly Val Leu Val Gln Pro Xaa
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(2)
<223> OTHER INFORMATION: X is an independently selected genetically or
      non-genetically-encoded amino acid other than Gly, and in the D
      conformation.

<400> SEQUENCE: 20

Xaa Xaa Val Leu Val Gln Pro Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(1)
```

```
<223> OTHER INFORMATION: X is an independently selected genetically or
      non-genetically-encoded amino acid other than Gly, and in the D
      conformation.
<220> FEATURE:
<221> NAME/KEY: X
<222> LOCATION: (8)..(8)
<223> OTHER INFORMATION: X is an independently selected genetically or
      non-genetically-encoded amino acid other than Gly, and in the D
      conformation.

<400> SEQUENCE: 21

Xaa Gly Val Leu Val Gln Pro Xaa
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(1)
<223> OTHER INFORMATION: X is an independently selected genetically or
      non-genetically-encoded amino acid other than Gly, and in the D
      conformation.
<220> FEATURE:
<221> NAME/KEY: G2
<222> LOCATION: (2)..(2)
<223> OTHER INFORMATION: G2 is in the D conformation.
<220> FEATURE:
<221> NAME/KEY: X
<222> LOCATION: (8)..(8)
<223> OTHER INFORMATION: X is an independently selected genetically or
      non-genetically-encoded amino acid other than Gly, and in the D
      conformation.

<400> SEQUENCE: 22

Xaa Gly Val Leu Val Gln Pro Xaa
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic polymer.
<220> FEATURE:
<221> NAME/KEY: X
<222> LOCATION: (1)..(2)
<223> OTHER INFORMATION: X is an independently selected genetically or
      non-genetically-encoded amino acid other than Gly, and in the D
      conformation.
<220> FEATURE:
<221> NAME/KEY: P7
<222> LOCATION: (7)..(7)
<223> OTHER INFORMATION: P7 is in the D conformation.
<220> FEATURE:
<221> NAME/KEY: X
<222> LOCATION: (8)..(8)
<223> OTHER INFORMATION: X is an independently selected genetically or
      non-genetically-encoded amino acid other than Gly, and in the D
      conformation.

<400> SEQUENCE: 23

Xaa Xaa Val Leu Val Gln Pro Xaa
1               5

<210> SEQ ID NO 24
<211> LENGTH: 9
<212> TYPE: PRT
<213> ORGANISM: Artificial Sequence
<220> FEATURE:
```

```
<223> OTHER INFORMATION: Synthetic polymer.

<400> SEQUENCE: 24

Gly Gly Cys Val Leu Val Gln Pro Gly
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 25

Cys Gly Gly Val Leu Val Gln Pro Gly Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 26

Cys Gly Gly Gly Gly Val Leu Val Gln Pro Gly Cys
1               5                   10
```